United States Patent
Roh et al.

(10) Patent No.: US 9,771,310 B2
(45) Date of Patent: Sep. 26, 2017

(54) STYRENATED PHENOL USEFUL AS CURING AGENT OR PLASTICIZING AGENT FOR EPOXY RESIN

(71) Applicant: KOREA KUMHO PETROCHEMICAL CO., LTD., Seoul (KR)

(72) Inventors: Kee Yoon Roh, Daejeon (KR); Jung Hee Jang, Daejeon (KR); Jin Eok Kim, Daejeon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 107 days.

(21) Appl. No.: 14/380,820

(22) PCT Filed: Nov. 25, 2013

(86) PCT No.: PCT/KR2013/010723
§ 371 (c)(1),
(2) Date: Aug. 25, 2014

(87) PCT Pub. No.: WO2015/076440
PCT Pub. Date: May 28, 2015

(65) Prior Publication Data
US 2016/0207859 A1   Jul. 21, 2016

(51) Int. Cl.
| | | |
|---|---|---|
| *C09D 163/00* | (2006.01) | |
| *C09D 7/12* | (2006.01) | |
| *C07C 39/04* | (2006.01) | |
| *C07C 39/15* | (2006.01) | |
| *C08G 59/62* | (2006.01) | |
| *C08L 63/00* | (2006.01) | |
| *C08K 5/13* | (2006.01) | |
| *C08G 59/50* | (2006.01) | |
| *C08G 59/24* | (2006.01) | |

(52) U.S. Cl.
CPC ............ *C07C 39/15* (2013.01); *C08G 59/245* (2013.01); *C08G 59/50* (2013.01); *C08G 59/621* (2013.01); *C08K 5/13* (2013.01); *C09D 7/1233* (2013.01); *C09D 163/00* (2013.01)

(58) Field of Classification Search
CPC ...... C07C 39/15; C08G 59/50; C08G 59/504; C08G 59/62; C08G 59/621; C08L 63/00–63/10; C09D 163/00–163/10; C09D 7/1233; C09J 163/00–163/10; C08K 5/13

See application file for complete search history.

(56) References Cited

U.S. PATENT DOCUMENTS

| | | | | |
|---|---|---|---|---|
| 2007/0292620 | A1* | 12/2007 | Volle | ................. C08G 18/6685 427/386 |
| 2012/0010330 | A1* | 1/2012 | Dettloff | .................. C08G 59/56 523/466 |
| 2012/0172493 | A1 | 7/2012 | Dettloff et al. | |

FOREIGN PATENT DOCUMENTS

| | | |
|---|---|---|
| CN | 102549041 A | 7/2012 |
| EP | 0335674 A1 | 10/1989 |
| JP | 57008221 A | 1/1982 |
| JP | 1-238549 A | 9/1989 |
| JP | 05132544 A | 5/1993 |
| JP | 09-025349 A | 1/1997 |
| JP | 2002-348530 A | 12/2002 |
| JP | 2003-193024 A | 7/2003 |
| JP | 2008088348 A | 4/2008 |
| JP | 2013-506030 A | 2/2013 |
| KR | 20110070081 A * | 6/2011 |
| WO | 2012/043213 A1 | 4/2012 |
| WO | 2013154785 A1 | 10/2013 |

OTHER PUBLICATIONS

SI Group, Mono-Styrylphenol (MSP-75) Technical Data Sheet (Feb. 2009).*
Partial machine translation of KR 20110070081 A.*
Huntsman Corporation, Jeffamine D-230 Polyetheramine Technical Bulletin (2008).*
International Search Report for PCT/KR2013/010723 dated Aug. 18, 2014.
Written Opinion of the International Searching Authority dated Aug. 18, 2014.

\* cited by examiner

*Primary Examiner* — Kregg Brooks
(74) *Attorney, Agent, or Firm* — Hauptman Ham, LLP

(57) ABSTRACT

The present invention relates to styrenated phenol useful as a curing agent or a plasticizing agent for an epoxy resin. More particularly, it relates to use of styrenated phenol, which has viscosity and curing properties similar to those of nonylphenol and exhibits superior curing properties for an epoxy resin, as a curing agent or a plasticizing agent for an epoxy-cured paint.

3 Claims, No Drawings

STYRENATED PHENOL USEFUL AS CURING AGENT OR PLASTICIZING AGENT FOR EPOXY RESIN

TECHNICAL FIELD

The present invention relates to styrenated phenol useful as a curing agent or a plasticizing agent for an epoxy resin.

BACKGROUND ART

Having superior performance in mechanical properties, electrical properties, thermal properties, chemical resistance, adhesivity, etc. when cured, epoxy resins are used in a wide range of applications including paints, electrical and electronic insulators, adhesives, etc.

Also, owing to superior physical properties such as hardening strength, hardness, sunlight resistance, processability, etc. and lack of the risk of evaporation of volatile substances or shrinkage during curing, epoxy resins are often used in paints coated on concrete materials after being mixed with suitable curing agents. When compared with other types of paints used for concrete protection, epoxy-cured paints are suitable because of less shrinkage and high mechanical and chemical resistance.

Meanwhile, nonylphenols are used in various industrial applications, including curing agents or plasticizing agents for epoxy-cured paints, owing to their intrinsic physical and chemical properties. However, as nonylphenol is known to induce renal toxicity and disrupt endocrine hormones, its industrial use is gradually prohibited or restricted. Especially in Europe, use of nonylphenol is prohibited entirely or restricted not to exceed 0.1% in products in some applications since 2003. EU Directive 2003/53/EC and EU REACH also regulate and control nonylphenols in the same way [Annex 17, REACH]. Also in Korea, use of nonylphenol is prohibited entirely in some products since January, 2010.

However, the related industries find difficulties due to the lack of materials that can replace nonylphenol. To replace nonylphenol, physical and chemical properties equivalent or comparable to those of nonylphenol are necessary.

Inspired by the fact that the viscosity and hardening properties of styrenated phenol are similar to those of nonylphenol, the inventors of the present invention investigated the possibility of use of styrenated phenol as an alternative to nonylphenol as a curing agent or a plasticizing agent for an epoxy resin.

Styrenated phenol is prepared from alkylation of phenol with styrene. Styrenated phenols may exist as monostyrenated phenol (MSP) having one styrene bonded to the benzene ring of phenol, distyrenated phenol (DSP) having two styrenes bonded and tristyrenated phenol (TSP) having three styrenes bonded. Although the styrenated phenols are commonly used as antioxidants for synthetic rubbers or resins, use of styrenated phenol as a curing agent or a plasticizing agent for an epoxy resin has not been reported yet.

DISCLOSURE

Technical Problem

The present invention is directed to providing a use of styrenated phenol as a curing agent for an epoxy resin.

The present invention is also directed to providing a use of styrenated phenol as a plasticizing agent for an epoxy resin.

The present invention is also directed to providing an epoxy paint containing styrenated phenol as a curing agent or a plasticizing agent.

Technical Solution

In an aspect, the present invention provides a curing agent or a plasticizing agent for an epoxy resin, containing styrenated phenol represented by Chemical Formula 1:

[Chemical Formula 1]

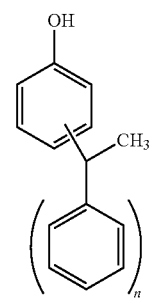

wherein n is 1, 2 or 3.

In another aspect, the present invention provides an epoxy paint containing: a main component containing an epoxy resin; and a curing agent containing the styrenated phenol represented by Chemical Formula 1.

Advantageous Effects

Since styrenated phenol has physical and chemical properties similar to those of nonylphenol and, in addition, can improve viscosity and facilitate curing, it can usefully replace nonylphenol. That is to say, styrenated phenol is useful as a curing agent or a plasticizing agent for an epoxy resin.

And, an epoxy paint containing a main component containing an epoxy resin and a curing agent containing styrenated phenol represented by Chemical Formula 1 is useful as a thick-film paint owing to superior adhesivity to concrete materials, less film shrinkage during curing and superior mechanical and chemical resistance of the cured film.

BEST MODE FOR CARRYING OUT INVENTION

The present invention provides use of styrenated phenol, which has viscosity and curing properties similar to those of nonylphenol, as a curing agent or a plasticizing agent when preparing an epoxy-cured paint.

The styrenated phenol according to the present invention may be represented by Chemical Formula 1:

[Chemical Formula 1]

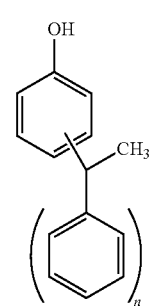

wherein n is 1, 2 or 3.

In the present invention, the styrenated phenol represented by Chemical Formula 1 with n=1 will be abbreviated as 'MSP', the compound with n=2 will be abbreviated as 'DSP', and the compound with n=3 will be abbreviated as 'TSP'.

As the styrenated phenol represented by Chemical Formula 1, MSP may include specifically 2-(1-phenylethyl)phenol (MSP-1) and 4-(1-phenylethyl)phenol (MSP-2).

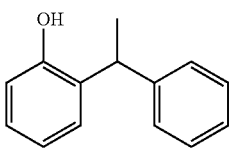

MSP-1

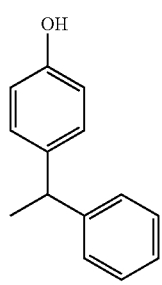

MSP-2

As the styrenated phenol represented by Chemical Formula 1, DSP may include specifically 2,4-bis(1-phenylethyl)phenol (DSP-1) and 2,6-bis (1-phenylethyl)phenol (DSP-2).

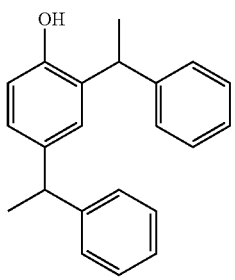

DSP-1

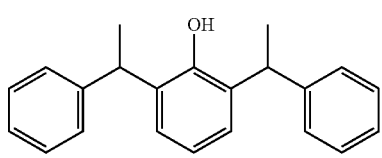

DSP-2

As the styrenated phenol represented by Chemical Formula 1, TSP may include specifically 2,4,6-tris(1-phenylethyl)phenol (TSP-1).

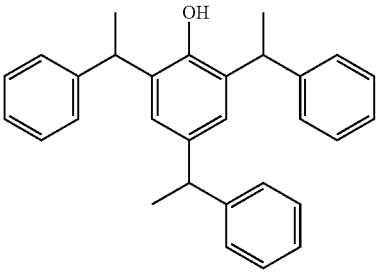

TSP-1

The styrenated phenol represented by Chemical Formula 1 is prepared by alkylating phenol with styrene by heating to 100-150° C. in the presence of an acid catalyst. Specifically, when 1 mol of phenol is reacted with 1-1.5 mol of styrene, a compound containing MSP, DSP and TSP at a ratio of MSP:DSP:TSP=50-75:15-35:1-8 (wt %) is produced.

The weight ratio of MSP, DSP and TSP is determined by the molar ratio of the phenol and the styrene used as reactants. The styrenated phenol may contain at least 50 wt %, specifically 50-75 wt %, of MSP. It is because viscosity is decreased as the content of MSP increases, providing good plasticity when being mixed with an epoxy resin, thereby providing good workability, and maintaining hydroxyl (OH) value the same as that of nonylphenol (240-250), thereby facilitating curing reaction.

The physical properties of styrenated phenol commercially available as the name Kumanox-3110 are compared in Table 1 with those of nonylphenol whose use is regulated.

TABLE 1

|  | Nonylphenol | Kumanox-3110 |
| --- | --- | --- |
| CAS No. | 84852-15-3 | 61788-44-1 |
| Structural formula | $C_{15}H_{24}O$ | Styrenated phenol (MSP content = 50-70%) |
| Weight-average molecular weight ($M_w$) | 220.3 | 220 |
| OH value | 240-250 | 240-250 |
| Viscosity (cps, 25° C.) | 1,000-1,200 | 400 |
| Color value (G) | 0.3 (Max 1.5) | 0.5 (Max 1.5) |
| Water content (%) | 0.1 (Max 0.2%) | 0.1 (Max 0.2%) |
| Note | Toxic | Non-toxic |

As can be seen from Table 1, styrenated phenol is a non-toxic, environment-friendly substance having weight-average molecular weight, hydroxyl (OH) value, viscosity, color value and water content very similar to those of nonylphenol. In particular, since styrenated phenol has lower viscosity than nonylphenol, plasticity is improved when mixing with an epoxy resin, thus providing excellent workability.

Accordingly, the styrenated phenol represented by Chemical Formula 1 can usefully replace nonylphenol as a non-toxic, environment-friendly substance.

The present invention also provides use of the styrenated phenol represented by Chemical Formula 1 as a curing agent for an epoxy paint which contains an epoxy resin as a main component.

Specifically, the epoxy paint may contain an epoxy main component and a curing agent. The main component of the epoxy paint contains an epoxy resin, a non-reactive diluent, a plasticizing agent, etc., and the curing agent contains a curing accelerator, a plasticizing agent, etc. The composition of the epoxy paint is studied in various ways. The present invention does not specially limit the components of the epoxy paint and their contents. In the present invention, the styrenated phenol represented by Chemical Formula 1 is used in the curing agent of the epoxy paint as a curing agent or a plasticizing agent. Specifically, the curing agent containing the styrenated phenol may contain 1-40 wt % of the styrenated phenol as a curing agent or a plasticizing agent and 60-99 wt % of a commonly used epoxy curing agent. Although use of a polyether diamine-based curing agent as the epoxy curing agent is described in the Examples section, the present invention does not specially limit the epoxy curing agent.

When used in the two-component epoxy paint, the curing agent containing the styrenated phenol provides improved workability with low paint viscosity and decreased curing time and enhances durability by increasing surface hardness.

In general, 100 wt % of the epoxy main component is mixed with 1-40 wt % of the curing agent to form a cured film.

The present invention will be described in more detail through examples. The following examples are for illustrative purposes only and it will be apparent to those skilled in the art that the scope of this invention is not limited by the examples.

Physical properties were measured as follows.
[Measurement of Physical Properties]
1) Viscosity Viscosity was measured at 25° C. using a rotational viscometer (Brookfield HAT viscometer or Brookfield LV DVE 230 viscometer).

2) Color

Color was measured using a color meter (Nippon Denshoku OME 2000).

3) Amine Value

Amine value was measured by titrating with 0.1 N HCl.

4) Curing Time

Curing time was measured at room temperature with 100 g scale with 25° C. (50° C. (0.1) mercury thermometer) as a base point.

5) Shore Hardness

Hardness was measured using a hardness meter (e-Asker Durometer Super EX Type-D). The final hardness means the hardness of a sample cured by heating at 80° C. for 2 hours. The change in the hardness of a sample cured at room temperature with time was monitored.

EXAMPLES

Example 1

Preparation of Styrenated Phenol

Phenol (300 g) was heated to 140° C. after adding phosphoric acid ($H_3PO_4$) as a catalyst (1.876 g, 0.006 eq). Then, styrene (381.6 g, 1.15 eq) was slowly added dropwise for 120 minutes. During the addition of styrene, reaction temperature was increased from 140° C. to 170° C. Upon completion of the addition of styrene, reaction was conducted for one more hour at the same reaction temperature. To remove unreacted reactants, temperature was lowered to 110° C. and sulfuric acid ($H_2SO_4$) was added as a catalyst (0.02 g, 1-3 wt % based on the phosphoric acid catalyst). During the addition of sulfuric acid, the reaction temperature was increased to 125° C. After conducting reaction at the temperature for 30 minutes, the temperature was lowered to 80° C. and the reaction mixture was neutralized for 30 minutes by aqueous adding sodium carbonate solution equivalent to the sulfuric acid used. The produced salts were removed by filtering after removing water through concentration under reduced pressure to obtain styrenated phenol (reaction conversion ratio=97%, purity≥97%).

GC analysis revealed that the obtained styrenated phenol contained 67 wt % of MSP, 27 wt % of DSP and 6 wt % of TSP.

Example 2

Preparation of Curing Agent for Epoxy Paint 2-1) Curing agent (A) containing styrenated phenol 198 g of D-230 (Jeffamine, Kukdo Chemical, polyether diamine) and 102 g of the styrenated phenol prepared in Example 1 were added to a 500 -mL polyether container and stirred using a magnetic stirrer. When generation of heat was completed, temperature was raised to 70° C. and the mixture was further stirred for 30 minutes and sieved through a 100-mesh molecular sieve to obtain 300 g of a curing agent (A).

2-2) Curing agent (B) containing nonylphenol 198 g of D-230 (Jeffamine, Kukdo Chemical, polyether diamine) and 102 g of nonylphenol were added to a 500-mL polyether container and stirred using a magnetic stirrer. When generation of heat was completed, temperature was raised to 70° C. and the mixture was further stirred for 30 minutes and sieved through a 100-mesh molecular sieve to obtain 300 g of a curing agent (B).

A result of measuring the viscosity and amine value of the curing agents (A) and (B) prepared in Example 2 is shown in Table 2.

TABLE 2

| | Viscosity (cps) | Amine value | Judgment |
|---|---|---|---|
| Curing agent (A) | 55 | 305.9 | Physical properties |
| Curing agent (B) | 48 | 309.5 | are similar |

Test Example. Comparison of Physical Properties Of Epoxy Paints 100 parts by weight of an epoxy main component containing 90 wt % of KER-828 (Kumho P&B Chemical, epoxy resin) and 10 wt % of benzyl alcohol was mixed with 40 parts by weight of the curing agent prepared in 2-1) or 2-2) and then cured.

TABLE 3

| | | Curing agent | | |
|---|---|---|---|---|
| | | Curing agent (A) | Curing agent (B) | Judgment |
| Curing time | | 3 hr 10 min | 3 hr 25 min | Curing time is shorter for curing agent (A) |
| Shore hardness | Day 2 | 51 | 45 | Hardness is higher for curing agent (A) |
| | Day 5 | 79 | 76 | |
| | Day 7 | 85 | 84 | |

INDUSTRIAL APPLICABILITY

As described above, styrenated phenol has physical and chemical properties such as viscosity, amine value, etc. equivalent or comparable to those of nonylphenol and, when contained in a curing agent for an epoxy paint, it provides shorter curing time, higher hardness of a cured film and superior physical properties as compared to a curing agent containing nonylphenol, thereby providing improved workability and durability.

Accordingly, the styrenated phenol is useful as a curing agent or a plasticizing agent for an epoxy resin.

The invention claimed is:
1. A plasticizing agent for an epoxy resin, comprising:
a styrenated phenol represented by Chemical Formula 1; and
a polyether diamine,

[Chemical Formula 1]

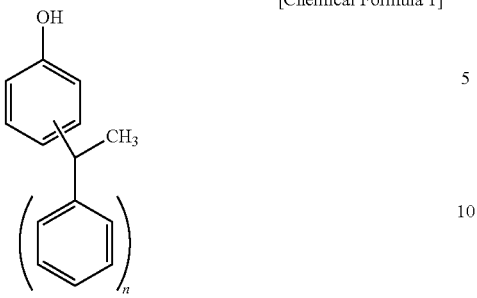

wherein the styrenated phenol comprises 50-67 wt % of monostyrenated phenol (MSP) with n=1, 15-35 wt % of distyrenated phenol (DSP) with n=2, and 6-8 wt % of tristyrenated phenol (TSP) with n=3, and n is 1, 2 or 3.

2. The plasticizing agent for an epoxy resin according to claim 1, wherein a weight ratio between the styrenated phenol represented by Chemical Formula 1 and the polyether diamine is about 102:198.

3. The plasticizing agent for an epoxy resin according to claim 1, wherein the polyether diamine is O,O'-Bis(2-aminopropyl)polypropylene glycol.

* * * * *